US009913755B2

(12) United States Patent
Pernot et al.

(10) Patent No.: US 9,913,755 B2
(45) Date of Patent: *Mar. 13, 2018

(54) ELASTIC BANDAGE THAT CAN BE USED, IN PARTICULAR, FOR THE TREATMENT AND PREVENTION OF VEIN DISEASES

(71) Applicant: LABORATOIRES URGO, Chenove (FR)

(72) Inventors: Jean-Marc Henri Maurice Pernot, Dijon (FR); Serge Lecomte, Dijon (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 161 days.

This patent is subject to a terminal disclaimer.

(21) Appl. No.: 14/425,586

(22) PCT Filed: Sep. 3, 2013

(86) PCT No.: PCT/FR2013/052027
§ 371 (c)(1),
(2) Date: Mar. 3, 2015

(87) PCT Pub. No.: WO2014/033419
PCT Pub. Date: Mar. 6, 2014

(65) Prior Publication Data
US 2015/0250654 A1    Sep. 10, 2015

(30) Foreign Application Priority Data

Sep. 3, 2012 (FR) .................................. 12 58186

(51) Int. Cl.
| | | |
|---|---|---|
| A61F 13/00 | (2006.01) |
| A61F 13/02 | (2006.01) |
| A61F 13/06 | (2006.01) |
| D04H 1/498 | (2012.01) |
| D04H 1/541 | (2012.01) |
| B32B 5/02 | (2006.01) |
| B32B 5/06 | (2006.01) |
| B32B 5/24 | (2006.01) |
| B32B 5/26 | (2006.01) |
| B32B 7/12 | (2006.01) |
| D04H 1/4382 | (2012.01) |
| A61F 13/538 | (2006.01) |
| A61L 15/24 | (2006.01) |
| A61L 15/26 | (2006.01) |
| A61L 15/42 | (2006.01) |
| D04H 1/46 | (2012.01) |

(52) U.S. Cl.
CPC .... *A61F 13/00017* (2013.01); *A61F 13/0273* (2013.01); *A61F 13/069* (2013.01); *A61F 13/538* (2013.01); *A61L 15/24* (2013.01); *A61L 15/26* (2013.01); *A61L 15/425* (2013.01); *B32B 5/022* (2013.01); *B32B 5/06* (2013.01); *B32B 5/245* (2013.01); *B32B 5/26* (2013.01); *B32B 7/12* (2013.01); *D04H 1/4382* (2013.01); *D04H 1/46* (2013.01); *D04H 1/498* (2013.01); *D04H 1/541* (2013.01); *A61F 2013/0028* (2013.01); *A61F 2013/00238* (2013.01); *B32B 2262/0253* (2013.01); *B32B 2262/0261* (2013.01); *B32B 2262/0276* (2013.01); *B32B 2262/062* (2013.01); *B32B 2262/12* (2013.01); *B32B 2266/0278* (2013.01); *B32B 2307/51* (2013.01); *B32B 2307/726* (2013.01); *B32B 2535/00* (2013.01)

(58) Field of Classification Search
None
See application file for complete search history.

(56) References Cited

U.S. PATENT DOCUMENTS

| | | | | |
|---|---|---|---|---|
| 4,100,324 A | * | 7/1978 | Anderson | ............ C11D 17/049 156/167 |
| 5,939,339 A | | 8/1999 | Delmore et al. | |
| 7,854,716 B2 | * | 12/2010 | Schuren | ................ A61F 13/069 602/53 |
| 2003/0040691 A1 | * | 2/2003 | Griesbach, III | .... A61F 13/0273 602/45 |
| 2004/0219854 A1 | * | 11/2004 | Groitzsch | ........... A61F 13/4902 442/328 |
| 2006/0148358 A1 | | 7/2006 | Hall et al. | |
| 2008/0269654 A1 | | 10/2008 | Chardon-Bras et al. | |
| 2010/0035500 A1 | * | 2/2010 | Kimura | ............... A61F 13/0273 442/353 |
| 2011/0208101 A1 | | 8/2011 | Keller et al. | |
| 2012/0122364 A1 | * | 5/2012 | Menczywor | ............ B32B 5/026 442/306 |

FOREIGN PATENT DOCUMENTS

| | | |
|---|---|---|
| EP | 0878179 | 11/1998 |
| EP | 2058424 | 5/2009 |
| EP | 2275062 | 1/2011 |
| FR | 2890854 | 3/2007 |
| JP | 2011-184846 | 9/2011 |
| JP | 2012-012758 | 1/2012 |
| WO | WO 2007/113430 | 10/2007 |
| WO | WO 2008/015972 | 2/2008 |

* cited by examiner

*Primary Examiner* — Kim M Lewis
(74) *Attorney, Agent, or Firm* — Hamre, Schumann, Mueller & Larson, P.C.

(57) ABSTRACT

A compression bandage formed by the assembling of a nonwoven based on short conjugate fibers which have been crimped and of a nonelastic material. The compression bandage can be used in a bilayer compression system, in particular for the prevention or treatment of venous pathologies.

21 Claims, No Drawings

ELASTIC BANDAGE THAT CAN BE USED, IN PARTICULAR, FOR THE TREATMENT AND PREVENTION OF VEIN DISEASES

The present invention relates to a novel compression bandage formed by the assembling of a nonelastic material and of a nonwoven obtained from short conjugate fibers, which have been crimped.

The invention also relates to the use of this bandage in a bilayer compression system, in particular for the prevention or treatment of venous pathologies.

The use of various compression systems has been known for a long time for treating pathologies of venous origin, such as, for example, venous insufficiency or the treatment of varicose veins and leg ulcers, or also for preventing venous thrombosis.

These systems are composed of one or more elastic bandages which apply a pressure to the limb to be treated.

The application of a suitable pressure has a favorable effect:
- on the one hand, on the vessels by reducing the diameter of the veins, which results in the acceleration of the blood flow and the reestablishment of the valvular function; and
- on the other hand, on the tissues by promoting better oxygenation and resorption of the edema.

In the treatment of chronic wounds and very particularly in that of leg ulcers, the use of a compression system—which makes it possible to reestablish or to promote normal venous circulation—is the reference treatment. This is the only therapy which has proved its effectiveness in treating and preventing the recurrence of wounds of this type.

An effective compression system must make it possible to meet four main objectives.

First, the system must be able to be worn continuously, day and night, for one or more days (for example a week) depending on the pathology, its seriousness or the therapeutic objective (treatment or prevention).

To this end, this system must thus make it possible to simultaneously apply:
- on the one hand, a relatively low pressure, known as "resting pressure", when the muscle is relaxed, in order to be comfortable and in particular endurable during the night; and
- on the other hand, a relatively high pressure, known as "working pressure", when the muscle is tensed or during movements, in particular during walking.

Secondly, the difference in pressure between resting pressure and working pressure must be sufficient to promote venous reflux.

Thirdly, the values for resting pressure, working pressure and difference in pressure must be stable over time.

Fourthly, the system must be easy and fast to put in place and in complete safety, in order to avoid tourniquet risks, if the pressure applied is too high, or risks of ineffectiveness, if the pressure or the difference in pressure is too low.

In order to achieve these objectives, knitted or woven elastic bandages, known as compression bandages, have been developed.

During its application around a limb, such as the leg, the bandage is stretched; depending on the degree of elongation, it applies, to the leg, a more or less high pressure. This pressure, which is the treatment pressure, depends mainly on two factors, the elongation of the bandage at being put in place and the circumference of the limb on which the bandage is applied.

The elastic compression bandages are thus wound at a given elongation around the leg. During the winding of the bandage, the latter is more or less completely covered over itself. Very often, this covering is 50% in the direction of transverse positioning of the bandage.

It is generally considered that a difference in pressure at 24 hours of between 15 and 25 mm of mercury is necessary in order to reestablish a correct venous flow. However, depending on the pathology, whether it is a treatment on legs without a serious ulcer, a difficult treatment on legs damaged by an edema or a treatment of a mixed arterial and venous ulcer, this range in values can extend from 10 to 35 mm of mercury, indeed even from 10 to 40 mm of mercury.

For ulcers, an applied working pressure at 24 hours of between 20 and 60 mm of mercury, depending on the pathology, is generally targeted.

In the case of the treatment of lymphedema, the important factor is more the applied pressure than the difference in pressure and for this pathology, for example for lymphedema of the leg, a working pressure at 24 hours of greater than 60 mm of mercury, preferably of between 65 and 100 mm of mercury, is targeted.

Manufacturers generally provide tables and ranges of products which, for a given limb diameter, make it possible to determine the pressure to be applied and to choose the appropriate system.

The compression bandages used are categorized by experts into two main categories, depending on the measurement of their elongation.

The classification is based on the measurement of the elongation as defined in the standard EN 14704-1 when the bandage is subjected to a maximum tensile force of 6 N/cm.

The conditions for carrying out the measurement are as follows.

A test specimen of the material to be tested with a width of 50 mm and a length of 250 to 300 mm is cut out and positioned without prestressing in the jaws of an electronic dynamometer (for example, a dynamometer of MTS brand), so as to have a width of 50 mm and a reference working length of 200 mm. The dynamometer stretches the test specimen at a rate of 100 mm/min up to a maximum force of 6 N/cm and then the crosspiece comes back to its initial position at the same return rate of 100 mm/min. This cycle is carried out 5 times and the elongation obtained in the fifth cycle, expressed as percentage, is directly calculated by the device. The operation is repeated on 5 test specimens and the mean value is taken.

1) "Short-Stretch" Bandages

On the basis of this test, taken as reference, a compression bandage is regarded as a "short-stretch" bandage if its elongation is less than or equal to 100%.

These bandages exert a low resting pressure and a high working pressure. They thus have a large difference in pressure, in particular during movements, for example during walking.

However, short-stretch bandages have many disadvantages.

First of all, they are difficult to put in place as small variations in elongation at being put in place generate strong increases or decreases in the pressure achieved and in the difference in pressure obtained. There thus exists a tourniquet risk if the pressure applied is too high or a risk of ineffectiveness if it is insufficient.

A significant decrease over time in the applied pressure and in the difference in pressure between working pressure and resting pressure and often slipping of the compression bandage is also observed.

This results in the need to carry out frequent changes of these bandages and a corresponding increase in the cost of the treatment.

A short-stretch bandage is, for example, sold by Activa under the Actico® name. This bandage is wound over a padding bandage wound beforehand over the leg. The padding is intended to distribute the pressures at the surface of the limb and/or to protect, by its thickness, boney projections and to absorb possible exudates if the bandage is placed on an open wound, for example in the case of leg ulcers.

2) Long-Stretch Bandages

On the basis of the preceding test, taken as reference, a bandage is regarded as a "long-stretch" bandage if its elongation is greater than 100%.

These bandages are easier to put in place as they exhibit a greater extensibility. For this reason, variations in elongation while putting in place do not generate large variations in the applied pressure. The tourniquet risk is low.

On the other hand, these bandages result in low variations in pressure between resting and working and in a low variation in pressure during movements, for example during walking. They prove to be less effective than short-stretch bandages.

They also exhibit a degree of discomfort in the resting position if it is desired to impose a high pressure, hence the need to remove them at night due to the trouble caused.

Long-stretch bandages are, for example, sold by Thuasne, and Smith and Nephew respectively under the Biflex® and Proguide® names.

Multilayer systems have been developed in attempting to overcome these disadvantages.

All the compression systems used today are composed either of a single bandage chosen from these two categories or of the combination of several bandages chosen from these two categories, if necessary in combination with a first padding layer in contact with the skin.

The most effective compression systems sold today are bilayer systems. Such a system is, for example, sold by Laboratoires Urgo under the K2® name. In this system, the pressure is distributed over the two elastic bandages and is applied mainly on the first bandage. The first bandage (sold under the Ktech® name) is a padding needled to an elastic knitwear and the second bandage (sold under the Kpress® name) is a self-adhesive elastic bandage consisting of a woven coated with latex. This system makes it possible to optimize the retention over time of the pressure and of the difference in pressures which is applied.

However, the industrial manufacture of this first bandage is complex.

This is because the assembling of the elastic bandage with the nonelastic material, such as the padding, is always problematic as the nonelastic material modifies the properties of the elastic bandage, in particular its lengthening.

The product resulting from this assembling may, in the worst of cases, become nonelastic or its lengthening may be considerably modified. Thus, the lengthening of the knitwear significantly decreases after needling with the padding.

It would thus be desirable to have available an elastic bandage, composed of an elastic material assembled with a nonelastic material, the properties of lengthening of the elastic material of which after assembling are not modified.

By working on a better optimization of the effectiveness of this compression system, in particular in order to improve the retention over time of the pressures applied and of the difference in pressures between resting pressure and working pressure, the inventors have succeeded in developing a novel elastic bandage, which can be used in particular as first bandage in a bilayer system, the properties of lengthening of which after assembling are not modified. Furthermore, unexpectedly, this bandage exhibits compression properties which are even more optimized, which make possible better retention of the pressures over time and the difference in pressure of which increases over time.

The assembling of a very specific nonwoven, manufactured from short conjugate fibers which have been crimped, with a nonelastic material, the thickness of which is greater than 1.8 mm and preferably between 1.8 and 4 mm and in particular between 2 and 3 mm, makes it possible to obtain a novel elastic bandage which is easily industrialisable and which has noteworthy properties, in particular for the treatment of pathologies of venous origin.

Extensible nonwovens are described in the patent application WO 2008/015972 for their use as compression bandage or taping bandage. The bandages described in this document are nevertheless too weak for their application as compression bandage to be able to be envisaged. This is because a compression bandage has to be sufficiently robust to withstand repeated deformations, rubbing actions and tightening actions for several days, mainly at the heal and malleolus. The compression bandages composed of nonwovens described in the application WO 2008/015972 can be perforated too easily and cannot be used in the field of compression therapy as compression bandages.

These nonwovens correspond neither to long-stretch bandages nor to short-stretch bandages. This is because, if an attempt is made to measure their elongation according to the standard EN 14704-1, which characterizes compression bandages, they break from the first cycle before having reached the maximum tensile force of 6 N/cm.

The applicant has obtained, by the assembling of such a nonwoven and of a nonelastic material which exhibits a thickness of greater than 1.8 mm, preferably between 1.8 and 4 mm, a product which exhibits noteworthy properties which render it particularly suitable for use in compression therapy.

It is thus found that a product is obtained which makes it possible to obtain, with such a bandage, better results—in terms of maintenance of the pressure applied and of the difference in pressure over time—than the first bandage of the bilayer compression system used today.

Contrary to what might have been expected, in the light of the weakness of these specific nonwovens, it is found that it is possible to assemble this product with another material without destructuring them or weakening them even more, but also without damaging their properties of extensibility and of self-adhesion.

On the contrary, surprisingly, their longitudinal extension properties are retained or improved, despite the assembling with a nonelastic material.

The present invention thus relates to a compression bandage comprising a nonelastic material, which exhibits a thickness of greater than 1.8 mm and preferably between 1.8 and 4 mm, and a nonwoven of crimped fibers obtained from short conjugate fibers, said nonelastic material and said nonwoven being assembled together and the nonwoven having a grammage of between 70 $g/m^2$ and 300 $g/m^2$, said crimped fibers being uniformly crimped in the direction of the thickness of the nonwoven and exhibiting a mean radius of curvature of between 10 and 200 micrometers and the number of crimped fibers at the surface of the nonwoven being greater than 10 crimped fibers/$cm^2$.

The present invention thus relates to a compression bandage comprising two nonwovens which were obtained from short conjugate fibers, the two nonwovens being assembled together. The bandage can be elastic and self-adhesive without comprising latex. Advantageously, the bandage can comprise less than 0.01% by weight of latex or of an adhesive of low adhesiveness while being self-adhesive.

The nonwoven and the nonelastic material can be assembled over the whole of their surface; the area and the shape of their surfaces can be identical or different. In the case where the compression bandage is used alone, it will be preferable for the nonwoven to exhibit a surface, in particular a length, which is greater than that of the nonelastic material in order to make it possible, at the end of the winding of the bandage, to attach the latter to itself by virtue of the self-adhesion of the terminal portion of the nonwoven which is not covered by the nonelastic material.

Nonwovens which can be used in the context of the present invention are described in the patent application WO 2008/015972.

Generally, the fibers which were used to manufacture the nonwoven are preferably conjugate fibers, of polymeric nature and noncontinuous (short).

The conjugate fibers within the meaning of the invention are fibers "having latent crimpability" possessed of an asymmetric or laminated structure which have the property of crimping under the effect of heating. They owe this property to the difference in thermal contraction coefficient of the polymers of which they are composed.

These fibers are advantageously composed of at least two polymers which exhibit a different thermal contraction coefficient. These polymers ordinarily have different softening points or melting points. They can be chosen from thermoplastic polymers, such as, for example: olefinic polymers (in particular $C_{2-4}$ polyolefin polymers, such as low-, medium- and high-density polyethylenes and polypropylenes), acrylic polymers (in particular acrylonitrile polymers having acrylonitrile units, such as acrylonitrile/vinyl chloride copolymers), vinyl acetal polymers (in particular polyvinyl acetal polymers), vinyl chloride polymers (in particular polyvinyl chlorides, vinyl chloride/vinyl acetate copolymers and vinyl chloride/acrylonitrile copolymers), vinylidene chloride polymers (in particular vinylidene chloride/vinyl chloride copolymers and vinylidene chloride/vinyl acetate copolymers), styrene polymers (in particular heat-resistant polystyrenes), polyester polymers (in particular poly($C_{2-4}$ alkylene arylate) polymers, such as polyethylene terephthalate, polytrimethylene terephthalate, polybutylene terephthalate and polyethylene naphthalate polymers), polyamide polymers (in particular aliphatic polyamide polymers, such as polyamides 6, 6-6, 11, 12, 6-10 and 6-12, semiaromatic polyamide polymers or aromatic polyamide polymers, such as polyphenylene isophthalamide, polyhexamethylene terephthalamide and poly(para-phenylene terephthalamide)), polycarbonate polymers (in particular polycarbonates of bisphenol A type), poly(para-phenylene-benzobisoxazole) polymers, polyphenylene sulfide polymers, polyurethane polymers, cellulose polymers (in particular cellulose esters), and the like. These thermoplastic polymers can optionally comprise other copolymerizable units.

When heating of the fibers is carried out with high-temperature steam, according to the preferred embodiment of the nonwoven, preference is given to polymers which are nonadhesive under wet heat (or heat-resistant hydrophobic or water-insoluble polymers), with a softening point or melting point of greater than or equal to 100° C., such as, for example, polypropylene polymers, polyester polymers and polyamide polymers. These polymers make it possible to prevent the bonding of the fibers by melting or softening of the fibers. Preference is very particularly given to aromatic polyester polymers and polyamide polymers, for their excellent stability, their resistance to heat and their ability to form fibers.

According to a preferred form of the present invention, the fibers used are bicomponent fibers. Bicomponent fibers can be composed of polymers of the same chemical family or of polymers of different chemical families, provided that they have different thermal contraction coefficients.

In one embodiment, the short conjugate fibers are bicomponent fibers, the two components making them up being polymers which exhibit a softening point of greater than or equal to 100° C., said polymers being chosen from polypropylene polymers, polyester polymers and/or polyamide polymers and preferably being two different aromatic polyester polymers.

It is preferable for the bicomponent fibers to be composed of two polymers of the same chemical family: for example of a homopolymer and of a copolymer. This is because it is possible to lower the degree of crystallinity of the homopolymer, indeed even to render it amorphous, or to lower its melting point or its softening point by copolymerizing the monomer with another. The difference in melting point or softening point of the two polymers can be, for example, of the order of 5 to 150° C., preferably of 50 to 130° C. and more preferably of 70 to 120° C. The proportion of copolymerizable monomer, with respect to the total amount of monomers, is, for example, of the order of 1 to 50 mol %, preferably of 2 to 40 mol % and more preferably of 3 to 30 mol % (particularly of 5 to 20 mol %). The ratio by weight of the homopolymer to the copolymer can be chosen as a function of the structure of the fibers; it is, for example, in terms of homopolymer (A)/copolymer (B) ratio, of the order of 90/10 to 10/90, preferably of 70/30 to 30/70 and more preferably of 60/40 to 40/60. In a preferred embodiment, the bicomponent fibers are composed of two aromatic polyester polymers and in particular of the combination of a polyalkylene arylate homopolymer (a) and of a polyalkylene arylate copolymer (b). The polyalkylene arylate homopolymer (a) can be a homopolymer of an aromatic dicarboxylic acid (in particular a symmetrical aromatic dicarboxylic acid, such as terephthalic acid or naphthalene-2,6-dicarboxylic acid) and of an alkanediol component (in particular ethylene glycol or butylene glycol). Use is made, for example, of a polymer of the series of the polyalkylene terephthalates, such as polyethylene terephthalate (PET) or polybutylene terephthalate (PBT), and ordinarily a PET with an intrinsic viscosity of the order of 0.6 to 0.7 used in the manufacture of ordinary PET fibers. The polyalkylene arylate copolymer (b) can be obtained from a first monomer used in the preparation of the polyalkylene arylate homopolymer (a) and a second monomer chosen from a dicarboxylic acid, such as an asymmetric aromatic dicarboxylic acid, an alicyclic dicarboxylic acid or an aliphatic dicarboxylic acid, an alkanediol component having a longer chain than the alkanediol of the polyalkylene arylate polymer (a), and/or a diol carrying an ether bond.

It is possible to use just one or to combine several of these second monomers. Among these components, use is preferably made of:

an asymmetric aromatic dicarboxylic acid, in particular isophthalic acid, phthalic acid or 5-sulfoisophthalic acid sodium salt, or an aliphatic dicarboxylic acid, in particular an aliphatic $C_{1-12}$ dicarboxylic acid, such as adipic acid, an alkanediol, in particular 1,3-propanediol, 1,4-butanediol, 1,6-hexanediol or neopentyl glycol, a polyoxyalkylene glycol, in particular diethylene glycol, triethylene glycol, polyethylene glycol or polytetramethylene glycol.

The choice is preferably made, among them, of in particular an asymmetric aromatic dicarboxylic acid, such as isophthalic acid, and a polyoxyalkylene glycol, such as diethylene glycol. The polyalkylene arylate copolymer (b) can optionally be an elastomer having hard alkylene arylate (ethylene terephthalate, butylene terephthalate) segments and having soft segments, for example of (poly)oxyalkylene glycol. In the polyalkylene arylate copolymer (b), the proportion of dicarboxylic acid component intended to lower the melting point or the softening point, with respect to the total amount of dicarboxylic acid component, is, for example, of the order of 1 to 50 mol %, preferably of 5 to 50 mol % and more preferably of 15 to 40 mol %. The proportion of diol component intended to lower the melting point or the softening point, with respect to the total amount of diol component, is, for example, at most 30 mol % and preferably at most 10 mol %, for example of the order of 0.1 to 10 mol %.

The cross section (section perpendicular to the direction of the length of the fibers) of the bicomponent fibers is not limited to the round shape (the ordinary shape of solid fibers) and to the modified shapes (flat, elliptical, polygonal, 3- to 14-foliated, T-shaped, H-shaped, V-shaped, "dog bone"-shaped (i-shaped), and the like) but can also be a hollow section. However, normally the round section is chosen.

Mention may be made, for the transverse structure of the bicomponent fibers, of the phased structures formed by a plurality of polymers, such as, for example, the structures of core-shell, islands and sea, mixed, parallel (side by side or multilayer laminate), radial (radial laminate), hollow radial, block or random types. Preference is given, among these structures, for a more spontaneous development of the thermal crimping, to a structure of eccentric core-shell type or of parallel type. In the case of bicomponent fibers of core-shell type and for example of eccentric core-shell type, the core can be composed of a polymer of the vinyl alcohol family, such as an ethylene/vinyl alcohol copolymer or a polyvinyl alcohol, or of a thermoplastic polymer with a low melting point or low softening point, for example a polystyrene or a low-density polyethylene, provided that it allows the crimping by the fact of having a difference in thermal contraction coefficient with the polymer constituting the shell.

In a specific embodiment, the bicomponent fibers have a structure of side by side type and are composed of a first polymer which is a polyethylene terephthalate and of a second polymer which is a copolymer of an alkylene arylate with isophthalic acid and/or diethylene glycol.

The mean count of the short conjugate fibers, in particular bicomponent fibers, can, for example, be between 0.1 and 50 dtex, preferably between 0.5 and 10 dtex and more preferably between 1 and 5 dtex (particularly between 1.5 and 3 dtex). If the count is too fine, not only are the fibers difficult to manufacture but there is a risk that they will lack strength. Furthermore, in the crimping stage, it is difficult to obtain beautiful coil-shaped crimps. If the count is too large, the fibers become stiff and make it difficult to develop a sufficient crimping.

The mean length of the short conjugate fibers before the crimping can, for example, be between 10 and 100 mm, preferably between 20 and 80 mm and more preferably between 25 and 75 mm (particularly between 40 and 60 mm). If the fibers are too short, apart from the difficulty in forming the web of fibers, the entangling of the fibers is insufficient in the crimping stage and it is difficult to guarantee good properties of strength and of extensibility. If the fibers are too long, not only does it become difficult to form a web of fibers of uniform grammage but the fibers become excessively entangled during the formation of the web, to the point of mutually hindering each other at the time of the crimping and of preventing the development of the extensibility. Furthermore, in the invention, the choice of the fiber length within the abovementioned range makes it possible for a portion of the crimped fibers at the surface of the nonwoven to slightly emerge from said surface of the nonwoven and thus to improve the self-adhesiveness of the nonwoven, which will be touched upon later.

In one embodiment, the mean count of the short conjugate fibers is between 1 and 5 dtex, preferably between 1.5 and 3 dtex, and the mean length of the short conjugate fibers is between 10 and 100 mm and preferably between 40 and 60 mm.

The application of a heat treatment to these conjugate fibers has the effect of developing the crimping and of imprinting on them crimps in relief having the shape of coils (spiral shaped or "coil spring"-shaped). The mean radius of curvature of the crimped fibers within the meaning of the invention corresponds to the mean radius of curvature of the circles formed by the loops of the coils of the crimped fibers; it can be between 10 and 200 microns, for example between 10 and 250 microns, preferably between 20 and 200 microns, preferentially between 50 and 160 microns and more preferentially between 70 and 130 microns.

The mean radius of curvature of the crimped fibers can be determined by electron microscopy according to the following method. A micrograph (magnification ×100) of a section of nonwoven is taken with a scanning electron microscope (SEM). Among the fibers appearing on the photograph, the fibers forming at least 1 spiral turn (coil) are selected and their radius of curvature is determined as the radius of the circle drawn along the spiral (radius of the circle when the crimped fiber is observed in the direction of the axis of the coil). When the fiber forms an elliptical spiral, the radius of curvature is determined as the half-sum of the great and small diameters of the ellipse. In order to exclude the fibers which have developed an insufficient coil-shaped crimping and the fibers which appear elliptical because of an oblique observation of the spiral, the procedure has been restricted to the elliptical fibers with a ratio of great to small diameters of between 0.8 and 1.2. The measurement is carried out, on the SEM image, of an arbitrary section of nonwoven and the mean is determined with regard to a population of fibers n=100.

When the crimping is carried out with high-temperature steam, the nonwoven according to the invention has the characteristic that the crimping of the conjugate fibers oriented approximately parallel to the planar direction is developed in an almost uniform fashion in the direction of the thickness. In a section of nonwoven taken in the direction of the thickness, among the domains delimited by a division into three equal parts in the direction of the thickness, the number of fibers forming at least 1 spirally wound crimp turn is, for example, in the central part (internal layer), from 5 to 50 per 5 mm (length in the planar direction) and 0.2 mm (thickness), preferably from 10 to 50 per 5 mm (planar) and 0.2 mm (thickness) and more preferably from 20 to 50 per 5 mm (planar) and 0.2 mm (thickness).

As the majority of the crimped fibers have their axis oriented in the planar direction and as the number of crimps is uniform in the direction of the thickness, the nonwoven displays a high extensibility (without comprising rubber or elastomer) and good operational strength (without comprising adhesives).

In the present description, the term "domains delimited by a division into three equal parts in the direction of the thickness" is understood to mean the different domains obtained when the nonwoven is cut into three equal slices oriented perpendicularly to the thickness.

In the nonwoven, uniformity of the crimping in the direction of the thickness can be defined by the fiber incurvation ratio. The term "fiber incurvation ratio" is understood to mean the L2/L1 ratio of the length of the two-dimensionally stretched fiber L2 to the distance L1 of the two ends of the fiber in the crimped state. This fiber incurvation ratio (in particular in the central domain in the direction of the thickness) is, for example, of the order of at least 1.3 (for example of 1.35 to 5), preferably of 1.4 to 4 (for example of 1.5 to 3.5) and more preferably of 1.6 to 3 (particularly of 1.8 to 2.5).

When the fiber incurvation ratio is measured on the basis of electron micrographs of sections of the nonwoven, the fiber length L2 does not correspond to the length of the fiber which would be obtained if the crimped fiber were stretched and rectilinearized three-dimensionally. It corresponds to the fiber length on a photograph which is obtained when the fiber appearing crimped is stretched and rectilinearized two-dimensionally on the photograph. In other words, the fiber length on the photograph which is measured according to the invention is lower than the real fiber length.

When the development of the crimping is approximately uniform in the direction of the thickness, the fiber incurvation ratio is also uniform in the direction of the thickness. The uniformity of the fiber incurvation ratio can be evaluated by comparing, in a section taken in the direction of the thickness, the fiber incurvation ratios obtained in the different layers delimited by a division into three equal parts in the direction of the thickness. Thus, in a section taken in the direction of the thickness, the fiber incurvation ratios obtained in the different domains delimited by the division into three equal parts in the direction of the thickness all lie in the abovementioned range and the ratio of the minimum value to the maximum value of the fiber incurvation ratio in the different domains (ratio of the domain where the fiber incurvation ratio is minimum to the domain where it is maximum) is, for example, of the order of at least 75% (for example, of 75 to 100%), preferably of 80 to 99% and more preferably of 82 to 98% (particularly of 85 to 97%).

According to one embodiment, the nonwoven exhibits, in a section taken in the direction of the thickness, a fiber incurvation ratio of greater than or equal to 1.3 in each of the domains delimited by a division into three equal parts in the direction of the thickness and the ratio of the minimum value to the maximum value of the fiber incurvation ratio in the different domains is greater than 75%.

As concrete method for measuring the fiber incurvation ratio and its uniformity, it is possible to apply the method which consists in taking a micrograph of the section of the nonwoven with an electron microscope and in measuring the fiber incurvation ratio on domains chosen within the different domains of the division into three equal parts in the direction of the thickness. The measurement is carried out, in each of the upper (front domain), internal (central domain) and lower (back domain) layers, on domains which, in the direction of the length, are at least 2 mm and, in the direction of the thickness, are positioned close to the center of each layer and have the same thickness from one domain to the other. Furthermore, these measurement domains are parallel in the direction of the thickness and are defined so that each includes at least 100 fragments of fibers allowing the measurement of their incurvation ratio (of the order preferably of at least 300 and more preferably of 500 to 1000). After having defined these measurement domains, the fiber incurvation ratio of all the fibers located in the domain is measured and the mean value with regard to each measurement domain is calculated, and then the uniformity of the fiber incurvation ratio is calculated by comparing the domain showing the greatest mean value and the domain showing the smallest mean value.

The fiber incurvation ratio and its uniformity can be measured according to the following methodology. A micrograph (magnification ×100) of a section of nonwoven is taken with an electron microscope and, in a portion where the fibers appear on the photograph, the thickness is divided into three equal domains (front, internal and back layers) and, close to the center of each domain, measurement domains of at least 2 mm in the direction of the length and comprising at least 500 fragments of fibers which can be measured are defined. The inter-end distance (shortest distance) between the two ends of the fiber, on the one hand, and the fiber length (length of the fiber on the photograph), on the other hand, are measured on these domains.

Specifically, when one fiber end emerges at the surface of the nonwoven, it is selected as is as end for measurement of the inter-end distance; when one fiber end dives into the nonwoven, the diving limiting portion in the nonwoven (end on the photograph) is selected as end for measurement of inter-end distance.

Among the fibers imaged, those on which it is not possible to isolate a continuity of at least 100 μm are excluded from the measurement. The fiber incurvation ratio is calculated as the L2/L1 ratio of the fiber length L2 to the inter-end distance L1 of the fibers. The mean on each of the front, internal and back layers of the division into three equal parts in the direction of the thickness is then calculated. Finally, the uniformity of the fiber incurvation ratio in the direction of the thickness is calculated from the ratio of its maximum and minimum values in the different layers.

The principle of the method for measurement of the fiber length is illustrated in FIGS. 4-a and 4-b of the patent application WO 2008/015972.

FIG. 4-(a) illustrates the case of a fiber, one end of which emerges at the surface and the other end of which dives into the nonwoven. The inter-end distance L1 is in this instance the distance from one end of the fiber as far as the diving limiting portion in the nonwoven. Furthermore, the fiber length L2 is the length obtained when the portion of the fiber which can be observed (portion ranging from the end of the fiber as far as the diving portion in the nonwoven) is stretched two-dimensionally on the photograph.

FIG. 4-(b) illustrates the case of a fiber, both ends of which dive into the nonwoven. The inter-end distance L1 is in this instance the distance of the two ends of the portion emerging at the surface of the nonwoven (ends on the photograph). Furthermore, the fiber length L2 is the length obtained when the fiber in the portion emerging at the surface of the nonwoven is stretched two-dimensionally on the photograph.

For coil-shaped crimped fibers, the mean pitch of the coil is, for example, of the order of 0.03 to 0.5 mm, preferably of 0.03 to 0.3 mm and more preferably of 0.05 to 0.2 mm.

The nonwoven can also comprise fibers which are not bicomponent fibers. Mention may be made, among these additional monocomponent fibers, for example, of the fibers of polymers already mentioned above but also cellulose fibers, such as, for example, natural fibers (wood wool, sheep wool, silk, hemp), semisynthetic fibers (in particular acetate fibers, such as triacetate fibers) or regenerated fibers (rayon, lyocell). The mean count and the mean length of the monocomponent fibers are preferably identical to those of the bicomponent fibers. It is possible to use just one type or to combine several types of these monocomponent fibers. Among these monocomponent fibers, preference is given in particular to regenerated fibers, such as rayon fibers, to semisynthetic fibers, such as acetate fibers, to polyolefin fibers, such as polypropylene or polyethylene fibers, to polyester fibers and to polyamide fibers.

It is preferable to combine, with bicomponent fibers of a chemical family (for example polyester family), monocomponent fibers of the same chemical family.

The ratio by weight of the bicomponent fibers to the monocomponent fibers is, for example, of the order of 80/20 to 100/0 (for example of 80/20 to 99/1), preferably of 90/10 to 100/0 and more preferably of 95/5 to 100/0.

The nonwoven which makes up the bandage of the invention is advantageously devoid of elastomeric fibers. Such elastomeric fibers are generally long filaments or fibers obtained from thermoplastic materials, such as polyurethane, polyamide, styrene copolymers or polyester. They are generally obtained by the melt blown process and generally have a length of greater than 100 mm. The nonwovens are advantageously devoid of long fibers positioned in the longitudinal direction of the bandage.

The nonwoven can also comprise additives, such as stabilizing agents, UV screening agents, photostabilizers, antioxidants, antibacterials, deodorizing agents, fragrances, colorants, fillers, antistatic agents, flame retardants, plasticizers, lubricants or crystallization retardants. It is possible to use just one or several of these additives. These additives can both be supported at the surface of the fibers and present inside the fibers.

In order to be able to obtain a compression bandage with the desired properties, the choice will be made—among the nonwovens produced from the fibers and polymers described above—of a nonwoven which exhibits a grammage of between 70 and 300 $g/m^2$, preferably between 80 and 200 $g/m^2$ and more preferably between 90 and 150 $g/m^2$. The grammage can be measured according to the standard EN 9073-1.

The total grammage of the two nonwovens is, for example greater than 200 $g/m^2$, indeed even greater than 220 $g/m^2$. In one embodiment, the total grammage of the two nonwovens is between 220 and 300 $g/m^2$.

An excessively low grammage makes assembling impossible as there is a risk of the excessively weak product being destroyed during assembling and an excessively high grammage does not make it possible to obtain the desired compromise between the extensibility, tearability and self-adhesion characteristics.

The other mechanical properties of the nonwoven will preferably be as follows.

The thickness of the nonwoven will advantageously be between 0.25 and 5 mm, preferably between 0.4 and 2.5 mm and very particularly between 0.5 and 1.5 mm. The thickness can be measured according to the standard EN 9073-2.

The lengthening of the nonwoven, that is to say its elongation at break, will be, in the longitudinal direction, advantageously of between 60 and 200% and preferably between 90 and 130% and, in the transverse direction, of between 70 and 200% and preferably between 60 and 160%. The longitudinal and transverse lengthening can be measured according to the standard EN 9073-3. The test of this standard consists in measuring the elongation at break, expressed as percentage, which corresponds to the value of the lengthening. The test conditions in the longitudinal direction are as follows.

A sample of the material to be tested (for example the nonwoven) with a length of 300 mm and with a width of 50 mm is subjected to a tensile test using an electronic dynamometer in which the crosspiece moves at a rate of 100 mm/mn. The space between the jaws is adjusted to 200 mm and the width is that of the test specimen, i.e. 50 mm. The dynamometer automatically stops when the sample breaks and the device records the elongation at break. The test is repeated on three samples and the mean value is taken.

In the transverse direction, the measurement is carried out in an identical fashion, the length between the jaws being adapted to the width of the material to be tested; for example, with a material with a width of 10 cm, the length of the sample between the jaws is 6 cm.

The elasticity of the nonwoven, as defined in the standard EN 14704-1, that is to say its elastic recovery after an elongation of 30%, is preferably greater than or equal to 70% (for example between 70 and 100%) and preferably between 80 and 95%.

The principle of the standard EN 14704-1 is based on the measurement of the elastic recovery is as follows. The conditions of the measurement are as follows.

A test specimen (for example of compression bandage or nonwoven) with a width of 50 mm and a length of 200 mm is inserted into the jaws of an electronic dynamometer, which will carry out a series of 5 cycles, up to an elongation of 30%, of "loading-unloading" tension at a rate of 100 mm/mn. The elongation recovered, obtained in the fifth cycle, expressed as percentage, as defined in the standard, is automatically measured by the dynamometer. The measurement of the elastic recovery, expressed as percentage, is calculated according to the formula defined in the standard on the basis of this recovered elongation. The operation is repeated on three test specimens and the mean value is taken.

In the context of the present invention, a material is regarded as elastic if its elastic recovery is greater than or equal to 70%.

The self-adhesion of the bandage according to the invention is obtained by virtue of the presence of numerous fibers in the partially free state at the surface of the nonwovens, the surface fibers mutually entangling at the time of the superimposition of the bandage on itself. In order to obtain this self-adhesion property without detrimentally affecting the tearability and extensibility properties, the number of crimped fibers, in particular in the form of a coil or loop, at the surface of the nonwoven is advantageously greater than 10 crimped fibers/$cm^2$ and preferably between 10 and 50 crimped fibers/$cm^2$. For the preparation of a compression bandage, preference will be given to a number of crimped fibers at the surface of the nonwoven of between 10 and 35 crimped fibers/$cm^2$.

According to one embodiment, the nonwoven is composed of side by side bicomponent fibers based on aromatic polyester polymers, the nonwoven has a grammage of between 90 and 150 $g/m^2$ and the number of crimped fibers at the surface of the nonwoven is between 10 and 35 crimped fibers/$cm^2$.

The number of crimped fibers at the surface of the nonwoven can be determined as follows.

A micrograph (magnification ×100) of the surface of the nonwoven is taken with an electron microscope and the number of crimped fibers (fibers making at least one loop-shaped spiral turn or coil turn which are formed at the surface of the nonwoven) is counted over a unit area of 1 cm² of surface of imaged fibers. The measurement can be carried out at five arbitrary points and the mean number of looped fibers, rounded to the nearest unit, is calculated.

The characterization of the self-adhesion of the nonwoven is evaluated by the measurement of the peel strength of a sample of nonwoven folded over itself. This peel strength for the nonwovens which can be used within the context of the present invention varies between 0.02 and 0.5 N/cm and preferably between 0.025 and 0.1 N/cm.

The test for characterizing the self-adhesion consists in measuring the peel strength at 180° of a sample of material using an electronic dynamometer. This peel strength represents the value of the self-adhesion of the material. The conditions for carrying out the measurement are advantageously as follows.

A sample of nonwoven with a length of 60 cm and a width of 5 cm is folded over itself while leaving free the ends which will be used to attach it in the jaws of the electronic dynamometer. The two faces are brought into contact under the pressure of a weight equivalent to 1 kgf/cm. Peeling is carried out by adjusting the dynamometer to a rate of 300 mm/mn. The dynamometer directly gives the peel strength, expressed in N/cm. The test is repeated on three samples and the mean value is taken.

Nonelastic material is understood to mean any material which exhibits, after an elongation of 30%, an elastic recovery, as defined in the standard EN 14704-1, of less than 70%.

Surprisingly, it has been found that the assembling of a nonwoven with a nonelastic material, which exhibits a thickness of greater than 1.8 mm and preferably between 1.8 and 4 mm and very particularly of between 2 and 3 mm, makes it possible to retain the longitudinal lengthening of the nonwoven, indeed even to increase it.

This nonelastic material can make it possible, according to the pathology to be targeted or the uses envisaged, to adapt the absorption, dampening and conformability properties of the compression bandage.

The nonelastic material can be chosen from textile materials, cellular materials, films or their combinations.

Among textile materials, materials based on synthetic or natural fibers can be used. Mention may be made of wovens, nonwovens, knitwear, 3D knitwear and their combinations.

The nonelastic material is preferably chosen from absorbent textile materials, such as knitwear, wovens, nonwovens and their combinations.

This material will preferably be a dampening, absorbent and breathing material and preferably an absorbent nonwoven. The nonelastic material is preferably an absorbent nonwoven having a thickness of between 1.8 and 3 mm and preferably a padding.

Among absorbent nonwovens, the preferred materials are paddings. By way of example, these paddings can be composed of viscose, polyester, polyurethane, cotton or rayon fibers. Such paddings are, for example, the products sold by Urgo Limited, Activa or Smith and Nephew respectively under the K-Soft®, Flexi-Ban® and Soft-Ban® names.

In the context of the present invention, preference will very particularly be given to the K-soft® padding, which is composed of a mixture of 60% of viscose fibers and 40% of polyester fibers and which exhibits a thickness of 2.5 mm and a grammage of 75 g/m².

The nonelastic material can optionally comprise active agents which contribute to improving the healing of the leg ulcer or which make it possible to reduce the pain or the edema, or also antibacterial agents.

According to an alternative embodiment, it will be possible to introduce, into the nonelastic material, antibacterial fibers, for example silver fibers, or to impregnate the nonelastic material with an antibacterial, for example triclosan.

The compression bandage according to the invention is produced by assembling the nonelastic material and a nonwoven chosen from those as defined above.

Assembling is understood to mean any means which makes it possible to bond the nonwoven and the nonelastic material together, with the result that their simple superposition cannot be regarded as assembling.

Varied textile technologies, such as, for example, sewing, needling, ultrasound welding, laminating or setting using an adhesive can be used to carry out this assembling.

These technologies will be chosen according to the nature of the materials (nonwoven and nonelastic material) to be assembled, in particular their resistance to temperature and their mechanical strength.

The nonwoven and the nonelastic material are preferably assembled by needling, with an adhesive or by ultrasound.

One of the advantages of the bandages according to the invention is that assembling is carried out without any other materials (nonwoven or nonelastic material) being subjected to a prestressing. Excellent reproducibility during industrial manufacture is thus obtained as there is no fine adjusting to carry out.

This assembly will be carried out so as not to detrimentally affect the self-adhesion and extensibility properties of the nonwoven and to guarantee the absence of delamination of the product over time.

In order to guarantee the absence of delamination of the product, care will be taken that the delamination strength between the nonwoven and the nonelastic material is greater than 10 cN/cm and preferably greater than 25 cN/cm.

The principle of the measurement of the delamination is based on the method commonly known as T-type delamination in which the force necessary to delaminate the materials making up the compression bandage is measured. This delamination force can be measured according to the following protocol. A test specimen is cut out from a compression bandage with a width of 50 mm and a length of 300 mm. The end of this test specimen is delaminated manually over a length of 1 to 3 cm, so as to fix each delaminated end of the bandage in the jaws of a dynamometer. The measurement is carried out so that there is an angle of 90° between the compression bandage and the end of the bandage delaminated beforehand. The delamination force is measured using the electronic dynamometer in which the crosspiece is movable and moves at the rate of 300 mm/min. The dynamometer directly records this measured force, which is expressed in cN/cm. The test is repeated on 3 test specimens and the mean value is taken.

Preference will very particularly be given to assembling by needling and in particular to assembling by needling between a nonwoven with a grammage of between 90 and 150 g/m² and a padding with a grammage of between 2 and 3 mm.

Consequently, another subject matter of the present invention is a process for the manufacture of a compression bandage as described above in which the nonelastic material and the nonwoven of crimped fibers are assembled together by needling, preferably without prestressing the nonwoven of crimped fibers, that is to say without stretching the nonwoven prior to the needling.

Use may be made, as needling machine, of a Fehrer machine having a board comprising between 800 and 3000 needles per linear meter.

The choice will preferably be made of an output rate on the needling line of between 0.5 and 25 meters/minute, of a length of penetration of the needles of between 8 and 25 mm and of a needling density of between 10 and 50 punches/cm$^2$.

According to a preferred embodiment, in order to promote precise positioning in place by the nursing personnel, the compression bandage will be provided with a calibration means. This calibration means can be visual, such as, for example, a group of pictograms, uniformly spaced, printed on the bandage or produced by means of a calibration system. Information on the recommended elongations when the bandage is put in place can be provided with the calibration means. The calibration can be carried out by the nursing personnel in the form of a stencil. This type of stencil or the explanations necessary to manufacture it can be incorporated in the packaging of the bandage. A kit comprising several bandages of different compositions, of different widths, of different lengths and/or having different calibrations in order to apply specific pressures can be used.

When the kit is indicated for the treatment of leg ulcers, it can in addition comprise one or more dressings intended to be put in place over the wound before the bandage is put in place.

The bandages according to the invention can be used in the treatment and the prevention of pathologies of venous origin, in particular leg ulcers.

These bandages will preferably be used in a multilayer compression system and in particular as first bandage of a bilayer compression system. As a secondary consideration, for use for a short period of time, for example from 1 to 3 days, they can be used alone and their end attached to itself after winding using a clip or a piece of adhesive tape or, as indicated above, using the portion of the nonwoven which is not assembled with the nonelastic material.

Another subject matter of the invention is the use of a compression bandage as claimed in one of the preceding claims in a bilayer compression system and in particular as first layer.

The compression bandage of the invention makes it possible to obtain moderate, indeed even high, working pressures which are maintained over time. To date, it has been impossible to maintain high working pressures which are stable over time with short-stretch bandages. For their part, long-stretch bandages have not made it possible to obtain working pressures which are sufficient for the treatment of certain pathologies.

The performance of the compression bandages of the invention can be evaluated in terms of working and resting pressures applied and of difference in pressure, over time, by using the in vitro test device and method described in the patent application WO 2007/113430, page 17, line 26, to page 19, line 18.

According to this method, the bandage is put in place around a cylinder with a total cover of 100% and then the circumference of the cylinder is continuously varied at a set rate between a "resting" position (smallest diameter) and a "working" position (greatest diameter), in order to mimic muscle contraction. Pressure sensors measure, over time, the values of the resting pressures and working pressures.

The time difference between the working pressure and resting pressure measurements is 5 seconds and the frequency of the measurements of these two successive parameters is 0.2 Hz.

In order to test the compression bandages according to the invention, it is possible to determine the elongation at the putting in place of the bandage as a function of the desired working pressure, for example using the tension/break curve as defined in the standard EN 9073-3.

In order to appropriately put the bandage in place, the bandages can be calibrated using a stencil, as described in the patent application WO 2007/113430, page 13, line 18, to page 14, line 6. If necessary, the value of the percentage of elongation at being put in place can be refined by a few successive tests.

The "Max. Pressure at T0" value corresponds to the first working pressure recorded immediately after putting in place and "Delta at T0" corresponds to the difference in pressure between the first working pressure and the first resting pressure which are recorded immediately after putting in place. The "Max. Pressure at T24" and "Delta at T24" values correspond to the measurements recorded 24 hours after putting in place. The difference in each of these two values between T0 and T24 hours, "Max. Pressure (T0-T24)" and "Delta (T0-T24)", is calculated.

The loss in working pressure at 24 hours, "Loss in Max. Pressure T24", with respect to the working pressure at being put in place, is also calculated by determining the ratio of the variation "Max. Pressure (T0-T24)" to the "Max. Pressure at T0".

The compression bandages according to the invention advantageously exhibit a working pressure at 24 hours ("Max. Pressure at T24") which varies from 15 to 40 mm of mercury, for example from 20 to 35 mmHg.

In addition, the compression bandages of the invention exhibit an excellent retention of the pressure applied at being put in place after 24 hours. The large fall in this value is generally of the order of 25 to 40% after 24 hours for the short-stretch compression bands of the prior art and of the order of 20 to 25% for the two-layer systems of the prior art. Thus, the "Max. Pressure (T0-T24)" value of the compression bandages of the present invention is advantageously less than 20%, for example between 5 and 15%.

The value of the differences in pressure at 24 hours ("Delta at T24") of the bandages of the invention is advantageously between 5 and 30 mm of mercury, for example between 10 and 20 mm of mercury.

The bandages of the invention exhibit, entirely unexpectedly, a negative difference between the Delta after being put in place and the Delta at 24 hours ("Delta (T0-T24)"). This result is all the more remarkable as it is obtained by a slower fall in the working pressure (which guarantees the effectiveness of the system) than that in the resting pressure.

The compression bandage of the invention is advantageously such that, at a working pressure, "Max. Pressure at T0", equivalent to that of another compression system of the prior art, the loss in pressure at T24 is reduced, which makes it possible to change the bandage less often.

Various examples of bandages in accordance with the present invention will now be given.

EXAMPLES: COMPRESSION BANDAGES

Different materials were used to manufacture bandages.

1. Materials Used a) Nonelastic Material

The nonelastic material used is the Ks ft padding sold by Urgo Limited.

It exhibits a grammage of 75 g/m$^2$. It is manufactured by the conventional carding, napping and preneedling process from viscose fibers and polyester fibers in the proportion of 60%/40% by weight.

These fibers have the following characteristics:
Viscose fibers of 1.7 dtex and with a length of 50 mm
Polyester fibers of 3.3 dtex and with a length of 60 mm b) Nonwovens The examples use two different nonwovens, based on crimped asymmetric bicomponent fibers, manufactured according to the teaching of the patent application WO 2008/015972. They respectively carry the references SJJ 142 for nonwoven A and SJJ 146 for nonwoven B from Kuraray.

These two nonwovens are produced from the fiber, of side by side type, based on polyester copolymers from Kuraray, the reference of which is PN-780.

These two nonwovens exhibit the following properties and characteristics:

|  | Nonwoven A | Nonwoven B |
|---|---|---|
| Grammage (standard EN 9073-1) | 96 g/m² | 134 g/m² |
| Thickness (standard EN 9073-2) | 1.13 mm | 1.14 mm |
| Elasticity (standard EN 14704-1) | 86% | 87% |
| Longitudinal lengthening (standard EN 9073-3) | 117% | 104% |
| Transverse lengthening (standard EN 9073-3) | 111% | 65% |
| Self-adhesion* | 0.03 N/cm | 0.03 N/cm |
| Number of crimped fibers at the surface of the nonwoven** | 19/cm² | 27/cm² |

*measured according to the method described above
**measured according to the method described above 2. Assembling The bandages were assembled by needling.

The tests on assembling by needling were carried out on a Fehrer needling machine using a board comprising 2500 needles per linear meter.

The implementational conditions on the needling line are as follows:
Output rate on the needling line: 1 meter/minute
Penetration of the needles: 13 mm
Needling density: 20 punches/cm² with nonwoven A and 40 punches/cm² with nonwoven B.

The padding and nonwoven B or nonwoven A are combined before needling without prestressing the nonwoven.

Example 1 corresponds to the needling of nonwoven B and the padding and example 2 to the needling of nonwoven A and the padding.

The longitudinal lengthening properties, measured according to the standard EN 9073-3, of the bandages according to the invention, before and after needling, were compared with those of the first bandage Ktech®, which corresponds to the needling of a knitwear and of the same padding, of the K2® compression system.

The results are collated in table 1.

TABLE 1

| Example | Lengthening in % |
|---|---|
| Knitwear alone, comparative | 180 |
| Ktech ®, comparative | 93 |
| Nonwoven B | 104 |
| Example 1 | 124 |
| Nonwoven A | 117 |
| Example 2 | 118 |

The analysis of the table clearly shows the advantages of the combination of this type of nonwoven with a nonelastic material, such as the padding.

For the Ktech® bandage, 50% of the lengthening of the starting knitwear is lost after needling, whereas, for nonwoven A, the lengthening virtually does not change and, for nonwoven B, it is improved by 19%.

By way of comparison, nonwoven B was needled with two other nonelastic nonwovens, the product Sontara® 8004 from DuPont, the thickness of which is 0.25 mm and the elastic recovery of which is 25%, and the product Jettex1005® from Orma, the thickness of which is 0.37 mm and the elastic recovery of which is 18%.

It is found that these two materials do not make it possible to obtain an elastic bandage. This is because it is found that their combination, after needling with nonwoven B, results in a compression bandage which breaks, when the standard EN 14704-1 is applied, before reaching the elongation of 30%. The elastic recovery of the padding is lower, 17%, but, surprisingly, by virtue of its thickness of 2.5 mm, it makes it possible to obtain an elastic bandage.

3. Performance of the Compression Bandages

The performance of the bandage of example 1 was compared with that of the first compression bandage of the K2® system, the Ktech® bandage.

The performances of both these compression bandages were evaluated in terms of working and resting pressures and of difference in pressure over time.

The in vitro testing device and method described in the patent application WO 2007/113430, page 17, line 26, to page 19, line 18, was used. According to this method, the bandage is put in place around a cylinder with a total cover of 100% and then the circumference of the cylinder is continuously varied at a set rate between a "resting" position (smallest diameter) and a "working" position (greatest diameter), in order to mimic muscle contraction. Pressure sensors measure, over time, the values of the resting pressures and working pressures.

The time difference between the working pressure and resting pressure measurements is 5 seconds and the frequency of the measurements of these two successive parameters is 0.2 Hz.

In order to test the compression bandage of example 1, the elongation at the putting in place of the bandage was determined as a function of the desired working pressure, for example using the tension/break curve as defined on the basis of the standard EN 9073-3. According to Laplace's law, the elongation to be carried out corresponds to the desired pressure.

In order to appropriately put the bandage of example 1 in place, the bandage was calibrated using a stencil, as described in the patent application WO 2007/113430, page 13, line 18, to page 14, line 6. If necessary, the value of the percentage of elongation at being put in place was refined by a few successive tests.

The Ktech® bandage of the K2® commercial product is already calibrated.

Each of the bandages was put in place at a given elongation, expressed as percentage, which is shown in table 2.

The "Max. Pressure at T0" value corresponds to the first working pressure recorded immediately after putting in place and "Delta at T0" corresponds to the difference in pressure between the first working pressure and the first resting pressure which are recorded immediately after putting in place. The "Max. Pressure at T24" and "Delta at T24" values correspond to the measurements recorded 24 hours after putting in place.

The difference in each of these two values between T0 and T24 hours, "Max. Pressure (T0-T24)" and "Delta (T0-T24)", was then calculated.

The loss in working pressure at 24 hours, "Loss in Max. Pressure T24", with respect to the working pressure at being put in place, was also calculated by determining the ratio of the variation "Max. Pressure (T0-T24)" to the "Max. Pressure at T0".

The combined results obtained are collated in table 2.

TABLE 2

|  | Ktech ®, comparative | Example 1 |
|---|---|---|
| Elongation at being put in place | 55% | 15% |
| Max. Pressure at T0 | 31 | 30 |
| Delta at T0 | 15 | 14 |
| Max. Pressure at T24 | 23 | 27 |
| Delta at T24 | 12 | 16 |
| Delta (T0 – T24) | 3 | –2 |
| Max. Pressure (T0 – T24) | 8 | 3 |
| Loss in Max. pressure at T24 | 25.8% | 10% |

Interpretation of the Results

The analysis of the results of table 2 demonstrates another advantage, apart from the ease of industrial manufacture by virtue of the absence of decrease in the lengthening of the nonwoven after needling with the padding: this is the remarkable improvement in the performance of this bandage with respect to the Ktech®.

It is thus found that there is a loss in working pressure at 24 hours of only 10%, versus 25.8% for the Ktech®.

It is also found that the difference in pressure between working pressure and resting pressure does not decrease over time. It changes from 14 immediately after being put in place to 16 mm of mercury after 24 hours, versus 15 to 12 mm of mercury for the Ktech®.

On the contrary, it unexpectedly increases.

Thus, for the bandage of example 1, the difference in Delta between putting in place and 24 hours is negative: –2.

This result is all the more remarkable as it is obtained by a slower fall in the working pressure (which guarantees the effectiveness of the system) than that in the resting pressure.

The compression bandage according to the invention thus improves its effectiveness over time.

The compression bandages according to the invention thus make it possible to advantageously replace the first bandage in a bilayer compression system and to improve the effectiveness of this system while being easier to manufacture.

The invention claimed is:

1. A compression bandage comprising a nonelastic material, which exhibits a thickness of greater than 1.8 mm and a nonwoven of crimped fibers obtained from short conjugate fibers,
    said nonelastic material and said nonwoven of crimped fibers being assembled together and the nonwoven of crimped fibers having a grammage of between 70 g/m$^2$ and 300 g/m$^2$,
    said crimped fibers being uniformly crimped in a thickness direction of the nonwoven of crimped fibers and exhibiting a mean curvature radius between 10 and 200 micrometers, and a surface of the nonwoven of crimped fibers having between 10 and 50 crimped fibers/cm$^2$.

2. The compression bandage as claimed in claim 1, wherein the short conjugate fibers are bicomponent fibers that are made of two polymer components which exhibit a softening point greater than or equal to 100° C., and which are selected from the group consisting of polypropylene polymers, polyester polymers and polyamide polymers.

3. The compression bandage as claimed in claim 2, wherein the bicomponent fibers are composed of a first polymer which is a polyethylene terephthalate and of a second polymer which is a copolymer of an alkylene arylate with isophthalic acid and/or diethylene glycol.

4. The compression bandage as claimed in claim 2, wherein the two polymer components consist of two different aromatic polyester polymers.

5. The compression bandage as claimed in claim 1, wherein the short conjugate fibers have a mean count of between 1 and 5 dtex and a mean length of between 10 and 100 mm.

6. The compression bandage as claimed in claim 1, wherein the crimped fibers exhibit a mean curvature radius of between 50 and 160 microns.

7. The compression bandage as claimed in claim 1, wherein the nonwoven of crimped fibers has a grammage of between 80 and 200 g/m$^2$.

8. The compression bandage as claimed in claim 1, wherein the surface of the nonwoven of crimped fibers has between 10 and 35 crimped fibers/cm$^2$.

9. The compression bandage as claimed in claim 1, wherein the nonwoven of crimped fibers exhibits, in a cross-section taken parallel to the thickness direction thereof,
    a fiber incurvation ratio greater than or equal to 1.3, and
    a ratio between a minimum value of the fiber incurvation ratio and a maximum value of the fiber incurvation ratio greater than 75%,
    wherein said ratio and said fiber incurvation ratio are measured in three parts of the nonwoven of crimped fibers, each part corresponding to one third thereof in a cross-section taken perpendicular to the thickness direction of the nonwoven of crimped fibers.

10. The compression bandage as claimed in claim 1, wherein the nonelastic material is selected in the group consisting of textile materials, cellular materials, films and their combinations.

11. The compression bandage as claimed in claim 1, wherein the nonelastic material is chosen from absorbent textile materials.

12. The compression bandage as claimed in claim 11, wherein the absorbent textile materials comprise knitwear, wovens, nonwovens and their combinations.

13. The compression bandage as claimed in claim 1, wherein the nonelastic material is an absorbent nonwoven having a thickness of between 1.8 and 3 mm.

14. The compression bandage as claimed in claim 13, wherein the absorbent nonwoven comprises a padding.

15. The compression bandage as claimed in claim 1, wherein the nonwoven of crimped fibers and the nonelastic material are assembled by needling, with an adhesive or by ultrasound.

16. The compression bandage as claimed in claim 1, wherein the nonwoven of crimped fibers is composed of bicomponent fibers based on aromatic polyester polymers, the nonwoven of crimped fibers has a grammage of between 90 and 150 g/m$^2$ and the surface of the nonwoven of crimped fibers has between 10 and 35 crimped fibers/cm$^2$.

17. The use of a compression bandage as claimed in claim 1 comprising applying the compression bandage to a limb of a patient.

18. A process for the manufacture of a compression bandage as claimed in claim 1, wherein the nonelastic material and the nonwoven of crimped fibers are assembled together by needling, without prestressing the nonwoven of crimped fibers.

19. The compression bandage as claimed in claim 1, wherein the short conjugate fibers have a mean count of between 1.5 and 3 dtex and a mean length of between 40 and 60 mm.

20. The compression bandage as claimed in claim 1, wherein the crimped fibers exhibit a mean curvature radius of between 70 and 130 microns.

21. The compression bandage as claimed in claim 1, wherein the nonwoven of crimped fibers has a grammage of between 90 and 150 g/m$^2$.

* * * * *